US00RE37651E

(19) United States

(12) Reissued Patent

Wallstén et al.

(10) Patent Number: US RE37,651 E

(45) Date of Reissued Patent: Apr. 9, 2002

(54) APPARATUS FOR MEDICAL TREATMENT

(75) Inventors: Hans I. Wallstén, Denens; Jérome Duc, Corseaux, both of (CH)

(73) Assignee: Wallsten Medical S.A., Denams (CH)

(21) Appl. No.: 09/425,972

(22) PCT Filed: Mar. 19, 1993

(86) PCT No.: PCT/SE94/00208

§ 371 Date: Oct. 24, 1995

§ 102(e) Date: Oct. 24, 1995

(87) PCT Pub. No.: WO94/21203

PCT Pub. Date: Sep. 29, 1994

Related U.S. Patent Documents

Reissue of:

(64) Patent No.: 5,693,080
Issued: Dec. 2, 1997
Appl. No.: 08/525,557
Filed: Oct. 24, 1995

(30) Foreign Application Priority Data

Mar. 19, 1993 (SE) ..... 9300919

(51) Int. Cl.[7] ..... A61F 7/00

(52) U.S. Cl. ..... 607/105; 607/98; 607/114; 606/31

(58) Field of Search ..... 607/96, 98–99, 607/101–102, 105, 113, 116, 156; 600/36; 606/21–22, 27–28, 31; 623/1

(56) References Cited

U.S. PATENT DOCUMENTS 4,160,455 A * 7/1979 Law
4,709,698 A * 12/1987 Fogarty
4,758,223 A * 7/1988 Rydell
4,773,899 A * 9/1988 Spears
4,799,479 A * 1/1989 Spears
4,860,744 A * 8/1989 Johnson et al.
4,949,718 A * 8/1990 Neuwirth et al.
5,047,025 A * 9/1991 Taylor et al.
5,105,808 A * 4/1992 Neuwirth et al.
5,133,710 A * 7/1992 Carter et al.
5,151,100 A * 9/1992 Adele
5,159,925 A * 11/1992 Neuwirth et al.
5,330,518 A * 7/1994 Neilson et al.
5,460,628 A * 10/1995 Neuwirth et al.

FOREIGN PATENT DOCUMENTS

EP 0 253 677 * 1/1988
EP 0 333 381 * 9/1989
EP 0 370 890 * 5/1990
WO WO90/02525 * 3/1990
WO WO91/05528 * 5/1991
WO WO91/05580 * 5/1991
WO WO93/05737 * 4/1993

* cited by examiner

*Primary Examiner*—Eric F. Winakur
*Assistant Examiner*—Ryan Carter
(74) *Attorney, Agent, or Firm*—Burns, Doane, Swecker & Mathis, L.L.P.

(57) ABSTRACT

An apparatus for effecting hyperthermia in a narrow body cavity or duct including: a disposable first part (1) having an elongate distal section (5) intended to be inserted into the cavity or duct having a centrally located, heat-releasing element (22), which is either surrounded by an elongate housing (24) or is itself constituted by an elongate housing, and a flexible and/or elastic enclosure (23) surrounding the housing in a liquid-tight manner, further including a device for supplying energy to the heat-releasing element (22) and an axially operating first inlet (135) at the proximal part of the housing, an outlet (133) from the housing being arranged for the supply of heat-transmitting medium under pressure for expansion of the flexible enclosure (23) to accommodate and to exert a controlled pressure on surrounding walls of the cavity or duct, a second inlet (131) to the housing (24), and medium-actuating device (13, 19) for the expansion of the flexible enclosure (23) and for internal circulation of the medium through the housing (24); and a permanent non-disposable second part (51) having a drive (55, 75) for the device (13, 19) for expansion and for internal circulation, and a connection (43, 59; 41, 81) for releasably interconnecting the drive (55, 75) and the device means (13, 19) for expansion and internal circulation.

39 Claims, 5 Drawing Sheets

APPARATUS FOR MEDICAL TREATMENT

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to an apparatus for effecting hyperthermia in a narrow body cavity or duct. The invention is especially applicable to the treatment of the endometrium of the uterus. The treatment resides in a combination of the supply of heat to said body cavity or duct and simultaneous application of a controlled pressure on surrounding tissue.

2. Background Art

In the treatment of certain disorders in narrow body cavities or ducts the supply of heat is frequently used, the treatment residing in so called hyperthermia. For use in such treatment several apparatuses have been described including a special catheter employing a balloon attached to the distal end of the catheter. In the treatment of for example menorrhagia the distal end of the catheter including the balloon is inserted into the uterus cavity via vagina and cervix, the balloon being [them] *then* expanded using a pressure medium up to a suitable pressure. The catheter includes heat-releasing means, for example an electric resistance element, to which electric energy is supplied from the exterior via the catheter, the generated energy and the temperature being controlled in different ways (see for example PCT/US89/03916).

In copending application PCT/SE92/00645 there is described an apparatus for carrying out hyperthermia involving the use of a heat-releasing element which is of an inherently self-regulating type. Examples of such elements are elements based on materials of the PTC-type or ferromagnetic materials where the means for the supply of energy are based on magnetic induction. In accordance with said PCT-application the problem of creating sufficient power output while avoiding self-inhibition associated with a heating element of the self-controlling type has been solved by arranging the element in a surrounding elongate housing through which the heat-transmitting medium is forced through and around the element by efficient internal circulation. Such internal circulation around and through the heat-releasing element is generated by providing a reciprocating movement of a small quantity of the pressurized quantity of heat-medium.

For details concerning this background art reference is made to the above-identified patent application PCT/SE92/00645, the full disclosure of which is incorporated herein by reference.

In apparatuses as those described above the balloon catheter is thus connected to sources for the supply of a liquid medium, electric energy and means for the control of the temperature and the supply of energy. In the apparatus according the above-mentioned PCT-application no means for temperature control are necessary but means for the generation of a reciprocating movement of a small quantity of the liquid medium will be required.

In the device according to the above PCT-application the liquid medium transferring heat to the area to be treated is in the form of a sterile liquid enclosed in a catheter, the distal part of which carries a distensible enclosure or balloon intended to be inserted in for example a uterus cavity. Due to this arrangement it is clear that not only the exterior parts of the catheter but also the interior thereof must be capable of cleaning and sterilization after use in view of the fact that leakage can result in infection of the enclosed liquid and thereby also the catheter parts. Even if a catheter is of a disposable type and is disposed of after use the means connected to the catheter, such as the means for generating pressure and internal circulation, will have to be cleaned and sterilized after every use since they have been in contact with the liquid medium. Such cleaning and sterilization is a very complicated and expensive procedure.

SUMMARY AND OBJECTS OF THE INVENTION

The present invention has for an object to provide a system meeting and requirements as to sterility.

Another object of the invention is to provide an apparatus where any risk of contamination from a preceding treatment is excluded.

Yet another object of the invention is to eliminate the risk for contamination and transfer of infection at a low cost for each treatment.

Still another object of the invention is to enable control and adjustment of the optimum average pressure during the course of treatment.

A further object of the invention is to provide a system through which excessive pressures hazardous to the patient can be avoided.

These and other objects will be obtained in accordance with the present invention by an apparatus for effecting hyperthermia in a narrow body cavity or duct, said apparatus being composed of a first disposable part comprising all constructional details subject to contamination, and a permanent non-disposable second part comprising the equipment necessary for operating the apparatus.

Accordingly, the present invention provides an apparatus for carrying out hyperthermia in a narrow body cavity or duct, said apparatus comprising:

a disposable first part comprising an elongate distal section intended to be inserted into said cavity or duct comprising a centrally located, heat-releasing element, which is either surrounded by an elongate housing or is itself constituted by an elongate housing, and a flexible and/or elastic enclosure surrounding said housing in a liquid-tight manner, further including means for supplying energy to the heat-releasing element end an axially operating first inlet at the proximal part of the housing, an outlet from the housing being arranged for the supply of heat-transmitting medium under pressure for expansion of the flexible enclosure to accomodate and to exert a controlled pressure on surrounding walls to said cavity or duct, a second inlet to the housing, and medium-actuating means for said expansion of the flexible enclosure and for internal circulation of said medium through the housing; and a permanent non-disposable part comprising drive means for said means for said expansion and for internal circulation, and connecting means for unfastenably interconnecting said drive means and said means for expansion and internal circulation.

In a preferred embodiment of the apparatus of the invention said medium-actuating means comprise a first means for the expansion of the flexible enclosure and a second means for the internal circulation of the medium.

It is particularly preferred that said first means for the expansion of the flexible enclosure by introduction of heat-transmitting medium thereto is capable also of bringing the enclosure into a collapsed condition enabling withdrawal of the instrument from the body cavity or duct.

It is preferred that said second means involves the use of a reciprocating element creating a reciprocating motion to a determined quantity of pressurized medium. Said reciprocating element is suitably part of an injection syringe, although it is conceivable to use other types of reciprocating elements, such as a bellows or a deformable non-elastic container, as will be illustrated in the following description of preferred embodiments.

Said first means for the expansion of the flexible enclosure may likewise be constituted by an ordinary injection syringe, but also in this case the syringe can be replaced by other devices capable of performing the same function, which is also illustrated more in detail below.

For the creation of a reciprocating motion to said reciprocating element it is suitable to use a device comprising an eccentric capable of converting a rotary motion to a rectilinear motion.

Said means for expansion and for internal circulation can be either constituted by two different syringes separately operable for expansion on the one hand and for internal circulation on the other hand. As an alternative one and the same syringe can be used for providing both expansion and internal circulation, thus simplifying the construction.

According to still another aspect of the invention the apparatus can be supplemented with a pressure control system residing in a second distensible enclosure, the interior of which is in communication with the interior of said flexible enclosure, whereby any undesired pressure arising in the flexible enclosure will be released through distention of said second enclosure.

In such embodiment it is preferred that the second enclosure has a higher resistance to distention than the flexible enclosure associated with the distal part of the catheter.

In a preferred embodiment of such supplemented apparatus there is arranged a non-elastic container surrounding the second enclosure, and such container is suitably provided with means for controlling the pressure within the container and outside of the second enclosure. In this manner the level of release of an arising excessive pressure can be adjusted.

In the above-identified PCT/SE92/00645 application a number of embodiments relating to the internal circulation system are described. Furthermore, said application describes different types of heat-releasing elements, a preferred type being a heat-release element based on a PTC-material. For details regarding such features reference is made to said PCT-application.

BRIEF DESCRIPTION OF THE DRAWINGS

The invention will in the following be further described by exemplifying embodiments which, however, must not be construed to restrict the scope of protection except as defined in the appended claims. These embodiments are described in connection with the appended drawings, wherein:

DESCRIPTION OF PREFERRED EMBODIMENTS

Figure 1:
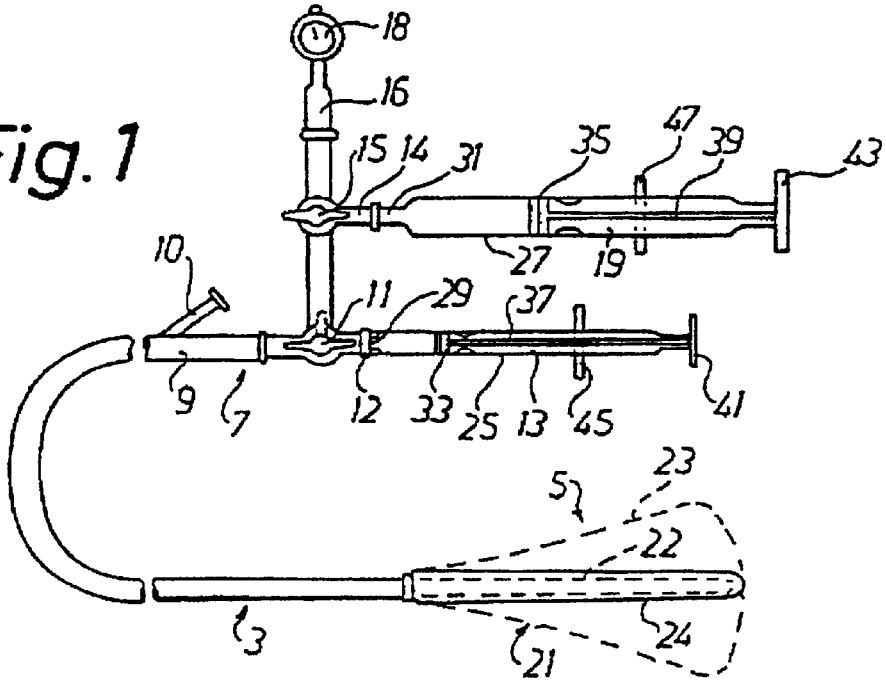
FIG. 1 diagramatic illustration of a disposable first part of an embodiment of the apparatus according to the invention.
Figure 2:
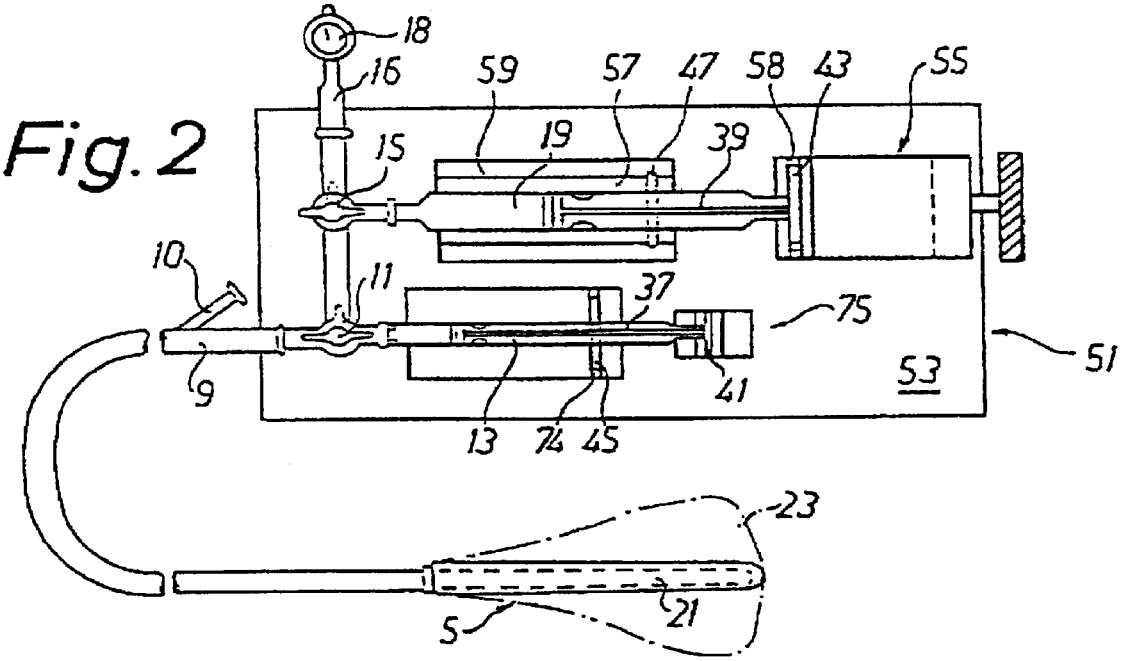
FIG. 2 is a diagramatic representation of combined disposable first part and permanent non-disposable part of the apparatus the present invention.

An embodiment of the apparatus according to the present invention is shown in full in FIG. 2, whereas the disposable first part thereof is shown in FIG. 1. Said disposable first part [5] *7* includes a catheter part 3 and a distal part 5 for the application of heat and pressure at the site of treatment, in the present embodiment the uterus cavity.

The distal part 5 includes a central body 21 comprising a housing 24 and harbouring a heat-releasing element 22, both having an elongate configuration. The central body 21 is surrounded by a thin flexible and elastic enclosure or balloon 23, which is distensible under the influence of a pressure medium supplied to the interior of said enclosure 23 in a manner to be illustrated below.

The disposable first part [5] *7* is furthermore provided with a proximal part comprising conduit means 9 with a first three-way valve 11 and a first attachment stud 12. As shown in FIGS. 1 and 2 conduit means 9 contains an access pipe 10 for the [accomodation] *accommodation* of electrical leads extending up to the heat-releasing element 22. Said leads are suitably connected to a voltage source, such as [rechargable] *rechargeable* low-volt batteries. Said conduit means 9 additionally includes a side-conduit 16 attached at its end to said first three-way valve 11 and including a second three-way valve 15 and an associated second stud 14. At the other end side-conduit 16 contains a leak-tight housing 18 having an elastic membrane to which a pressure sensor can be attached from the outside for pressure control purposes.

Proximal part 9 further includes two injection syringes 13,19 for a purpose to be described below. Each syringe 13,19 is provided with a housing or body 25 and 27, respectively, and their respective front dispensing ends 29 and 31, respectively, are leak-tightly connected to studs 12 and 14, respectively. Syringes 13,19 are furthermore provided with conventional pistons 33,35, respectively, each piston having its piston bar 37 and 39, respectively, and actuating plates or discs 41 and 43, respectively. Finally, syringe housings 25,27 are each provided with an outer circumferential flange 45 and 47, respectively.

As previously indicated FIG. 2 illustrates the assemble apparatus including the disposable first part 7 and a non-disposable part 51 for repeated use. Said non-disposable part 51 includes support or platform 53 onto which the different parts of the auxillary equipment are attached.

As seen in FIG. 2, syringe 19 is associated with drive means 55, whereas syringe 13 is associated with drive means 75.

Figure 4:
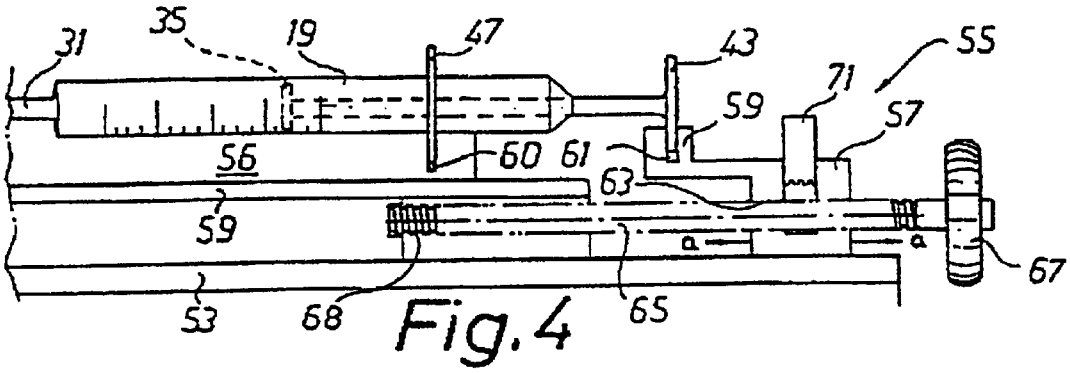
FIG. 4 is an enlarged side-view of another detail of the embodiment shown in FIG. 2.
Figure 5:
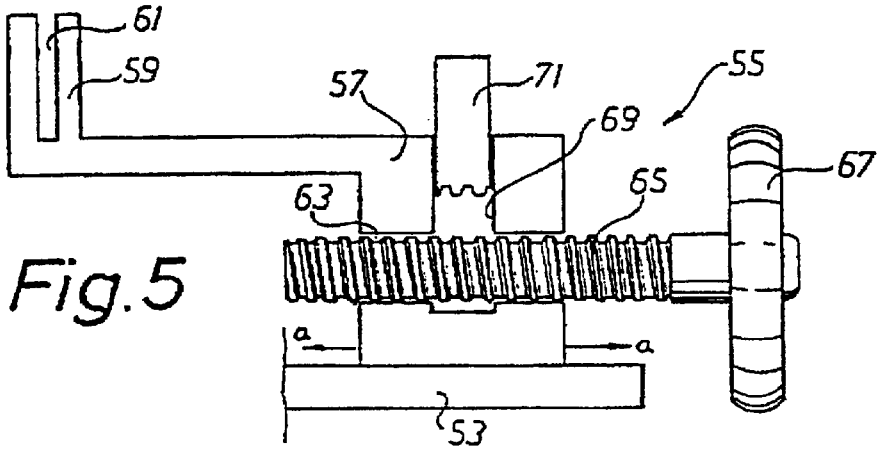
FIG. 5 is an enlarged side-view of a detail of the part shown in FIG. 4.

Referring now to FIGS. 4 and 5 drive means 55 for syringe 19 include a piston bar actuator 57 slideably mounted on platform 53 in the direction of arrows a). Actuator 57 includes a connecting element 59 with a slot 61 for receiving actuating plate or disc 43. Furthermore, actuator 57 contains a through-hole 63 for a threaded bar 65 having an operating nob 67 at its free end and rotatably but axially fixed at its other end. Finally, actuator 57 is provided with a side-opening 69 containing a radially displacable threaded element 71, the function of which is explained further below.

As seen in FIG. 4 syringe 19 is arranged on a bed 56 attached to a plate 59 which in turn through a spacer 68 is attached to platform 53. Bed 56 is provided with a slot 60 for receiving the outer circumferential flange 47 of syringe 19.

Figure 3:
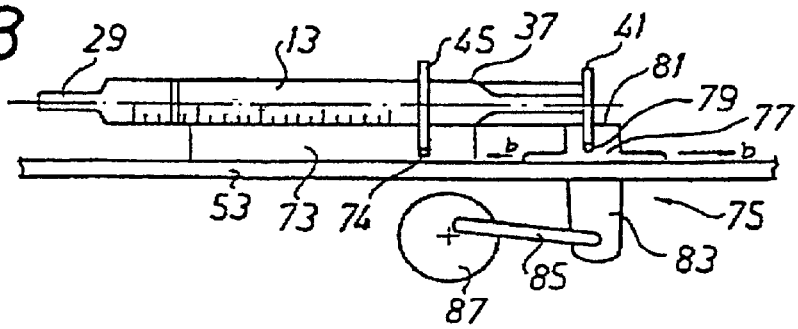
FIG. 3 is an enlarged side-view of a detail of the embodiment of FIG. 2.

FIG. 3 illustrates in more detail drive means 75 associated with syringe 13. Again, syringe 13 is arranged on a bed 73 attached to the upper side of platform 53 and is provided with a slot 74 for receiving the outer circumferential flange 45 of syringe 13. Said drive means 75 are provided with an actuator 77 for piston bar 37 of syringe 13. Actuator 77 is slideably mounted on platform 53 in the direction of arrows b), and has an upper part 81 provided with a recess or slot 79 for receiving actuating plate or disc 41 of syringe 13. Actuator 77 is furthermore provided with a lower part 83 linked to a rotating excenter disc 87 via an arm 85.

Figure 6:
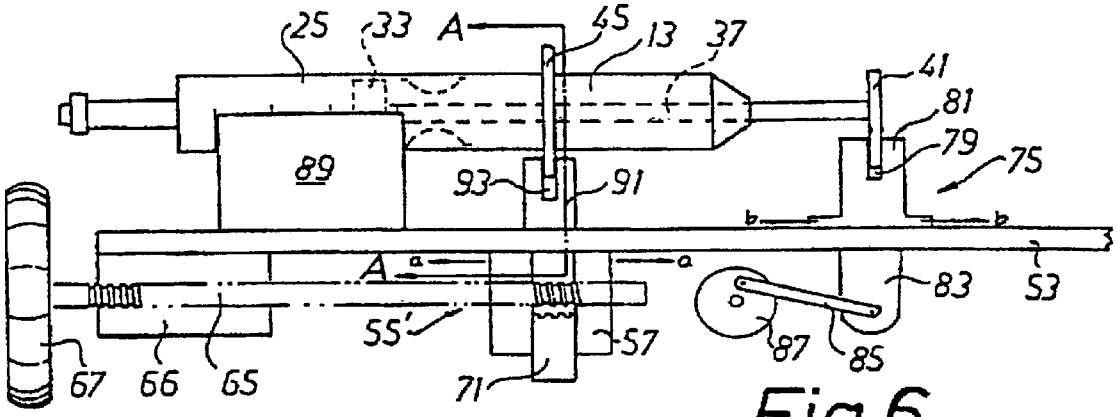
FIG. 6 is a side-view of an alternative arrangement using only one syringe for both expansion and internal circulation.
Figure 7:
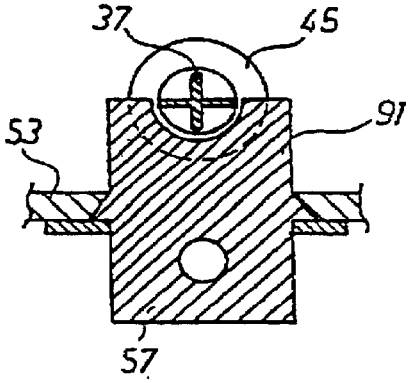
FIG. 7 is a section along line A—A of FIG. 6.

FIGS. 6 and 7 disclose an alternative embodiment of the apparatus of the inventions wherein syringes 13 and 19 are replaced by one single syringe capable of performing two functions as will be described in the operation of the apparatus below. This alternative arrangement according to FIGS. 6 and 7 has the single syringe 13 arranged axially slideable on a bed 89 and contains as before an outer circumferential flange 45. Drive means 75 correspond closely to those described in connection with FIG. 3.

In this alternative embodiment there is arranged an alternative drive means 55' largely corresponding to drive means 55 illustrated in detail in FIGS. 4 and 5 but performing the same function in a different manner. Drive means 55' are provided with an-upper part 91 extending above platform 53 and provided with a slot 93 receiving flange 45 of syringe 13. Its lower part 57 corresponds functions-wise to actuator 57 according to FIGS. 4 and 5. Actuator 57 with its upper part 91 is slideably arranged in platform 53 in the direction of arrows a). Threaded bar 65 is rotatably arranged but axially fixed in a block 66 attached To platform 53 underneath thereof. The remaining parts of drive means 55' are designed and perform in the same manner as described in relation to drive means 55 of FIGS. 4 and 5. FIG. 7 shows an illustrative cross-section along line A—A in FIG. 6.

Figure 8:
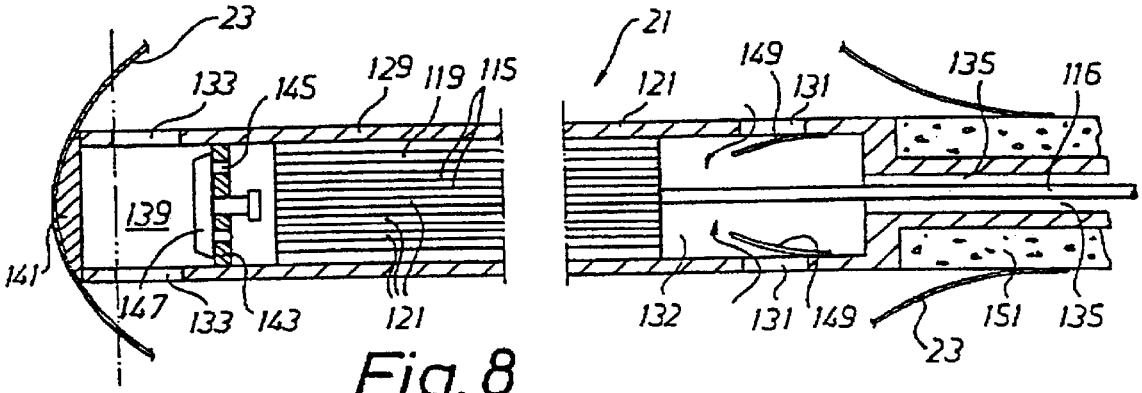
FIG. 8 shows in enlargement a longitudinal section through the central body 21 of the embodiment shown in FIGS. 1 and 2.
Figure 9:
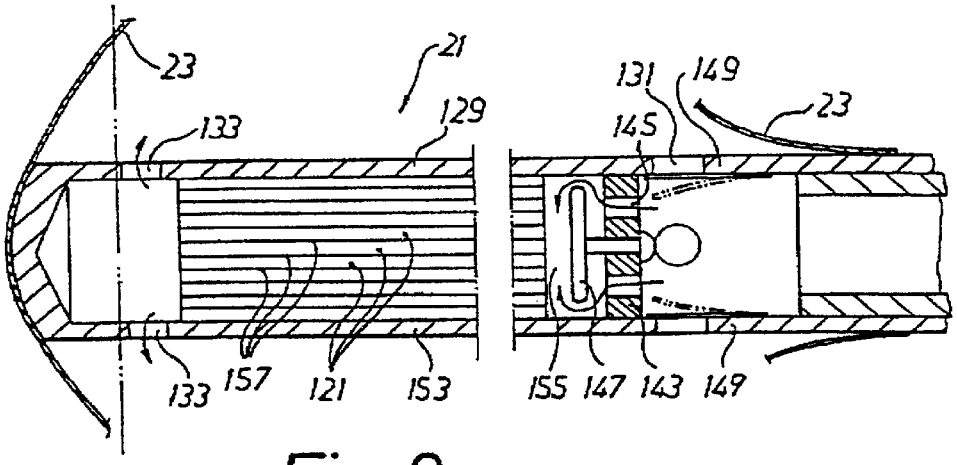
FIG. 9 shows a corresponding section of an alternative embodiment of the central body 21 of the embodiment shown in FIGS. 1 and 2.

FIGS. 8 and 9 show two embodiments of the central body 21 including the heat-releasing element 22 and the flexible or elastic enclosure or balloon 23 according to FIG. 1.

FIG. 8 shows a detail a system from enabling effective heat transport and heat transfer from the heat-emitting element 119 to the uterus mucosa (endometrium). Element 119 contains wires 115 for electrical resistance heating thereof. Wires 115 are supplied with electric energy via leads 116 entering through canal 135. Apertures 131 in the proximal part of the tubular central body operate as radially acting inlets for a pressurized liquid medium to a valve housing 132 communicating with an inlet canal 135, the space between central body 21 and enclosure 23, as well as with canals 121 arranged about and through the heat-emitting element 119 in the middle part of the central body 21. Apertures 133 arranged in the distal part of the central body 21 act as outlets for the pressurized liquid medium from a second valve housing 139 communicating with canals 121 and the space between the central body 21 and the elastic enclosure 23, said enclosure being liquid-tight sealed around the proximal part of the central body at 151 and being attached to a nose member 141 of the central body. In valve housing 132 back valves 149 are arranged so as to close apertures or openings 131 at over-pressure in the valve housing 132 and opening at a sub-pressure relative to the liquid pressure in the space between central body 21 and the elastic enclosure 23. A partition 143 having openings 145 is arranged in valve housing 139. A disc valve 147 is moveable in an axial direction and arranged so as to close openings 145 at over-pressure in valve housing 139 relative to the liquid pressure in canals 121 in the heat-emitting element of the central body or opening at sub-pressure in valve housing 145, respectively.

FIG. 9 shows in detail a central body 21 containing heat-releasing elements 157 of an inherently self-regulating type, such as PTC-material or ferromagnetic material having a Curie point. Element 157 also contains canals or passages 121, and said elements 157 and canals 121 are surrounded by a housing 29. In other respects the embodiment of FIG. 9 corresponds to that of FIG. 8 but with the difference that the disc valve 147 and the associated partition 143 with apertures 145 are now arranged in the proximal part of central body 21. Between the inlet side of the wires 153 and the partition 143 a chamber 155 is arranged.

FIG. 9 shows how the liquid medium is forced to circulate into chamber 145 and further in through the wire package 157 at a pressure shock at the same time as valves 149 close apertures 131.

The procedure for performing hyperthermia in a uterus cavity using the apparatus described above including the function of said apparatus will now be explained more in detail.

The disposable first part 7 can be stored in a sterile package separate from the stationary part up to the time of treatment when it is assembled with the stationary part 51 in the manner indicated above. Although said disposable first part 7 contains a number of elements performing the necessary functions for the operation of the apparatus according to the invention it is interesting to note that all parts thereof, in order to obtain a disposable assembly, can it be produced in large series at a direct cost not amounting to approximately more than between say 25 and 50 USD.

At preparation for treatment the syringe 19 is filled with somewhat more than the quantity of sterile liquid medium required to fill up the system and is then connected to stud 14. By maintaining the disposable part 7 in a vertical position with syringe 19 in a vertical uppermost position and imparting short movements to piston 35 of syringe 19 the system will be filled with liquid and at the same time air can be removed from the system and collected in syringe 19. Syringes 19 and 13 can easily be freed from air by disconnecting them from the system. Syringes 19 and 13 are then connected to their respective studs and piston of syringe 19 is positioned so that the enclosure 23 remains in a collapsed condition. The distal part 3 of the applicator is then inserted through vagina, cervix and into the uterus cavity up to the bottom of the cavity. The length of the central body 21 corresponds approximately to the length of the uterus cavity, i.e. normally 4 to 6 cm. Next, syringe 19 is attached with its operating end to drive means 55 by inserting disc 43 into slot 61. Syringe 13, partially filled with liquid, is attached with its rear operating end to drive means 75 by inserting disc 45 into slot 79. Three-way valves 11,15 are set so as to establish communication between syringes 19 and 13 and the interior of enclosure 23, and piston 35 is pushed forward within syringe 19 to expand the flexible enclosure 23 to conform to the surrounding uterus wall. Piston 35 is pushed forward until the desired pressure is reached as recorded by the pressure sensor.

As seen in FIGS. 4 and 5 drive means 55 can be used for free movement of piston 35 in syringe 19 by retracting threaded element 71 to the position shown in FIGS. 4 and 5. On the other hand, by pushing threaded element 71 into engagement with the threaded bar 65 fine adjustment of the position of piston 35 can be attained by rotating nob 67, whereby fine adjustment of the pressure in the system can be attained.

After the filling procedure drive means 75 are started imparting to the piston 33 of syringe 13 a reciprocating motion. At every positive pressure shock a certain volume of liquid is brought to move forward through the conduits up to the inlet canal 135 of the central body (FIG. 8). This has for an effect that simultaneously a corresponding quantity of pressurized liquid medium is forced through canals 121 in the central body 21 in view of the fact that valves 149 are closed at the same time as valve 147 is opened, and a corresponding quantity of pressurized liquid medium will be pushed out into the space inside the flexible enclosure 23.

At every subsequent backward movement of the piston of syringe 13 a corresponding quantity of liquid medium will be sucked back, valves 149 taking the open position shown in FIG. 8 and valve 147 its closed position. It is appreciated that under the influence of the oscillating pressure shocks and the described valve system a powerful and effective circulation in an internal flow circuit of liquid medium at the pressure given by syringe 19 will be provided through canals 121 of the central body 21 and out into the space within the balloon enclosure and back to the central body without hot liquid passing the inlet canal 135 of the catheter to the other parts of the apparatus. Thus, circulation takes place only in the distal part of the apparatus, whereas the inlet canal 135 during circulation only serves as a communication conduit for transmitting in a hydraulic manner the oscillating pressure and liquid movement provided by syringe 13 and for maintaining the desired pressure in the system by means of syringe 19.

In the treatment using the apparatus according to the present invention the pressure used in the system varies from case to case and may also vary during the treatment of one and the same patient, in view of for example variations in blood pressure, contractions of muscular tissue etc. A suitable pressure range lies within the interval between about 120 and about 170 mm Hg, and a suitable temperature of the circulating liquid is about 65° to 90° C. The period of treatment for obtaining the desired result varies within relatively wide limits but satisfactory results are usually obtained with a time of treatment varying from about 20 to about 30 min.

In order to obtain satisfactory internal circulation it has been found that a reciprocating frequency for the means for internal circulation lies between about 300 and 1000 strokes per min at a stroke volume of about 0.1 to 0.5 ml. It is to be noted that these values are to be considered only as suitable guidelines and other values lying outside of the ranges given are fully conceivable.

By considering the illustrations of FIGS. 1 and 2 it is appreciated that FIG. 2 shows the disposable first part 7 which, after use, can be disconnected from the non-disposable stationary part 51 and is then transferred to a destruction site so that infection through contamination can be avoided. The stationary part 51 will be completely free of any contamination and can be used repeatedly.

The stationary part 51 can additionally contain sources of electric energy, electrical leads and it can also contain a unit for the control of pressure, temperature and time and suitable displays for visualizing the corresponding parameters.

The embodiment shown in FIGS. 6 and 7 using only one syringe 13 for performing both filling and pulsating functions operates in a similar manner, although expanding the enclosure is performed by operating drive means 55' to move the body or housing 23 of syringe 13 relative to the piston 33 and the bed 89 in an axial direction. After the expanding operation the body 25 of syringe 13 is maintained in a fixed position by bringing threaded element 71 in engagement with the threaded bar 65, whereafter drive means 75 is started to perform the function of providing internal circulation in the same manner as the device shown in FIG. 3.

Figure 10:
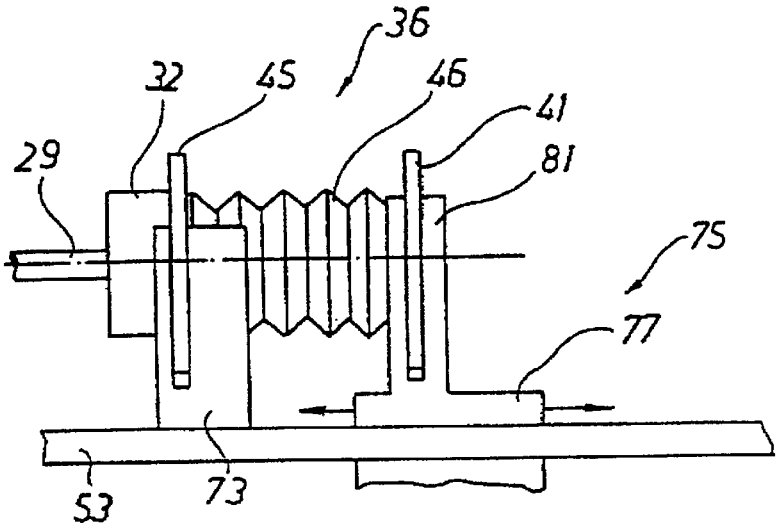
FIG. 10 shows a side-view of an embodiment alternative to that shown in FIG. 3.

FIG. 10 shows an arrangement which constitutes an alternative to the embodiment shown in FIG. 3. This alternative drive means 75 is arranged on platform 33, and syringe 13 of FIG. 3 has been replaced by a device 36 comprising an elongate hollow body 32 and, attached at the rear end thereof outside of flange 45, a bellows 46 which at its rear end in turn carries actuating plate or disc 41.

Operatively, the device of FIG. 10 operates in exactly the same manner as the arrangement described in connection with FIGS. 2 and 3 to provide for effective circulation in an internal flow circuit of liquid medium.

Figure 11:
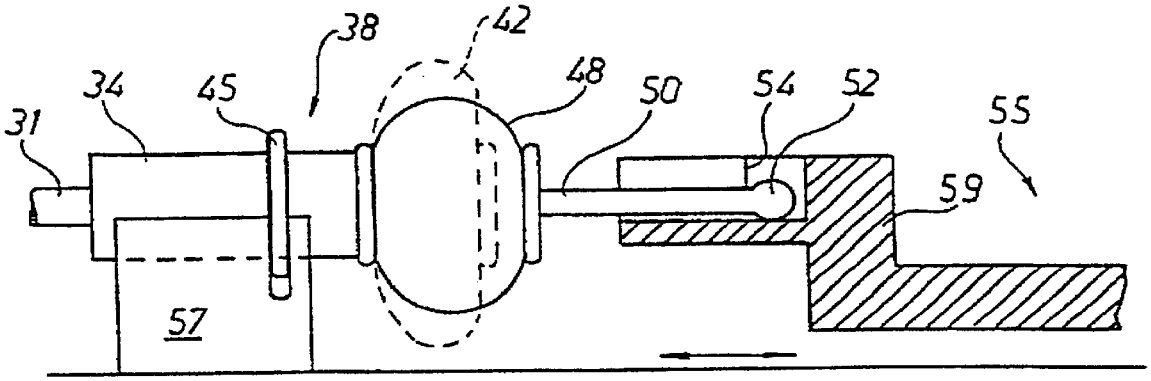
FIG. 11 is an embodiment alternative to that shown in FIG. 4.

In FIG. 11 there is shown an arrangement which constitutes an alternative to the embodiment shown in FIG. 10, where syringe 13 of FIG. 3 has been replaced by another device 38. Driving device 75 as shown in FIG. 3 is not illustrated in FIG. 11 except element 59 that has been modified to match new device 38 replacing syringe 19.

Device 38 contains a hollow elongate body 34 having an exterior circumferential flange 45 engaging a slot in bed 57 in the same manner as shown in FIG. 3. At the rear end of body 34 there is arranged a flexible inelastic container 48 which is connected to element 59 of drive means 55 through a bar 50 having at its free end a ball 52 fitting into a recess 54 of element 59.

The device shown in FIG. 11 can thus be used to replace syringe 13 shown in FIG. 2 using the eccentric device of FIG. 3 for providing reciprocation of element 59 resulting in internal circulation as previously described. In such pulsation, container 48 of FIG. 11 moves between the position shown in full line and the position shown in dotted line at 42.

Even if an indicated above there are alternative embodiments, wherein the syringe 19 and 13 according to FIG. 1 have been replaced with other devices illustrated in FIGS. 10 and 11, the embodiment according to FIG. 1 involving syringe 19 is preferred. On the one hand, such syringes can be massproduced at a very low cost and, on the other hand, as already described such a syringe can easily be deairated and filled with liquid, respectively, through an operation well known to the operator. Furthermore, syringe 19 can be graduated, such as with a milliliter scale, so that the operator will know the quantity of liquid injected into the system.

When using drive means 55' and 55', according to what has bee described in connection with FIGS. 4 and 5 and FIG. 6, respectively, fine adjustment of the system pressure can be made, and practice has also shown that this is necessary.

As earlier described the distal section 5 of the device, the enclosure being in a collapsed condition, is inserted into the uterus cavity, piston 35 of syringe 19 being then pushed forward to expand the enclosure. As long as the expansion takes place without the walls of the enclosure touching the walls of the cavity the expansion takes place at a low pressure depending inter alia on the elastic properties and thickness of the material of the enclosure. As a rule a highly elastic, thin enclosure material is desirable in order to obtain maximum compliance with the irregular inside surface contour of the uterus cavity while offering at the same time efficient heat transfer from the liquid medium to the endometrium.

Figure 12:
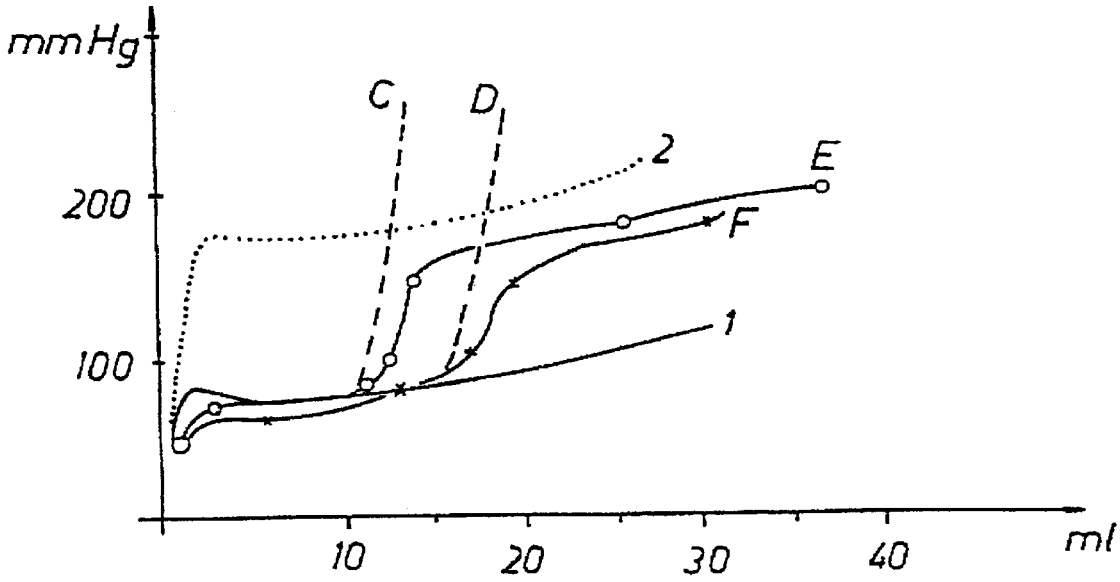
FIG. 12 shows a diagram on the present/volume relation in using a pressure control device.

To the extent that the enclosure in its expansion comes into engagement with the major part of the interior surface of the uterus cavity the resistance of the uterus muscle towards expansion will increase, the pressure in the system increasing at a higher rate for every volume of liquid injected. Pressure versus volume is indicated in FIG. 12. Curve 1 in full line shows said relation in the free expansion of a thin-walled elastic enclosure suitable for the treatment of uterus in accordance with the present invention. As seen from the figure a certain initial pressure (about 70 mm Hg) will be required for a first small expansion (about 1 ml). Then the expansion takes place at a slowly increasing pressure (about 70–100 mm Hg) that can be designated the plateau pressure. As earlier mentioned the curve will take another shape when the enclosure is brought to expand in for example a uterus cavity.

FIG. 12 shows two curves A-C and B-D with dashed lines the pressure/volume relation with two different cavity sizes. As seen from the figure the curves increase quite steeply depending on the resistance of the uterus muscle. According to the invention it is intended to open the cavity by expansion of the enclosure so that the whole interior surface of the cavity will be subjected to heat treatment at the same time as the circulation of blood will be reduced so that a more efficient and deeply penetrating heat destruction can be obtained. However, it is important that uterus will not be subjected to an excessive pressure which can cause damage through tissue failure. It has been found that a suitable pressure lies within the range about 100 to 140 mm Hg. Higher pressures can be used but the pressure should not exceed abouth 170 to 180 mm Hg. Even if for example such a device for fine adjustement of the pressure as described in connection with FIG. 4 will be used the steep increase in pressure at a small change of volume constitutes a problem, inter alia in view of the fact that the living muscle does not give a constant resistance. In certain cases strong contractions arise in the muscle, which could result in a drastic increase pressure if a rapidly acting pressure release cannot be provided.

It is conceivable to arrange for servo control of the device for fine adjustment as described so that the pressure can be maintained between two pre-determined values, but such system is complicated and is not always rapid enough in order to compensate for for example muscle cramps.

Figure 13:
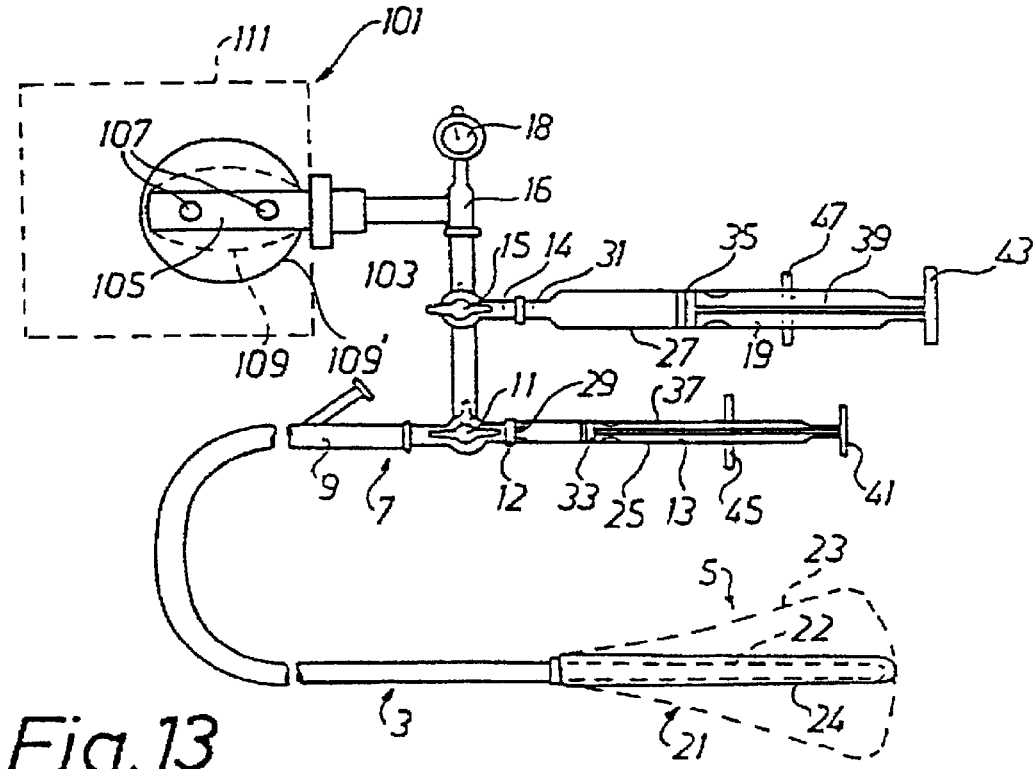
FIG. 13 shows an embodiment of the device of the invention harbouring such a pressure control system through which hazardous excessive pressures can be avoided.

FIG. 13 shows a pressure control device which in a simple and efficient manner provides for facilitated adjustment of pressure and enables pressure release upon sudden pressure increase resulting from for example contraction of uterus. Said control means designated 101 has been added to [=he] *the* disposable part 7 shown in FIG. 1, via a second side conduit 103 connected to side conduit 16 of the disposable part 7. Control device 101 contains a central tube 105 provided with holes 107. Said tube 105 is surrounded by an elastic balloon 109 which is thereby connected to the disposable part 3 so as to be filled with liquid when the system is filled using syringe 19. When pressurizing the system elastic balloon 109 then expands, such as to the position 109' shown in full line in FIG. 13.

In accordance with the invention there is selected for balloon 109 an elastic material of for example silicon. The plateau pressure of said material is substantially higher than the plateau pressure for enclosure 23 but somewhat higher or equal to the pressure suitable for the treatment.

The pressure/volume relation for a suitable material is shown in FIG. 12 by curve 12 in dotted line. As is clear from FIG. 12 the plateau pressure lies within the range about 180 to 200 mm Hg.

The system including pressure control device 101 is pressurized as described in connection with FIGS. 4 and 5, but the pressure/volume relation will be different in view of the fact that also balloon 109 will expand during the pressure increase.

FIG. 12 shows how the pressure increase AC changes to AE and how the pressure increase BD changes to BF. The change obtained by adding the pressure control device 101 to the system results on the one hand in the advantage that the pressure increase within the range 80 to 150 mm Hg is less steep, i.e. easier to control. On the other hand, the pressure increase at pressures exceeding about 160 mm Hg is very slow. In this case a suitable operating pressure is about 150 to 160 mm Hg. This means for example that at a sudden contraction of uterus the pressure increase from the pre-set pressure will be relatively small so that damages to uterus can be prevented. The reason as to why drastic pressure increase can be prevented is the fact that if enclosure 23 will be compressed through contraction of uterus a corresponding quantity of liquid will be transferred to balloon 109. If the contraction of uterus ceases a corresponding quantity will be transferred back from balloon 109 to enclosure 23.

As is clear from the above description the supplementary equipment residing in pressure control device 101 is simple [end] *and* cheap in manufacture and belongs to the part of the equipment that is disposed of after use.

In certain cases it can be of advantage to be able to vary the plateau pressure of the balloon 109. This can be done by surrounding balloon 109 with an airtight container 111 shown by the dashed square in FIG. 13. Container 111 can be provided with pressurizing means, such as a manual operated pump, not shown it FIG. 13. By pressurizing container 111 the plateau pressure of balloon 109 can be set at the desired value. In this manner different plateau pressures can be obtained using one and the same balloon 109.

We claim:

1. An apparatus for effecting hyperthermia in a body cavity or duct comprising:

a disposable first part comprising an elongate distal section intended to be inserted into said cavity or duct comprising a centrally located, heat-releasing element, which is either surrounded by an elongate housing or is itself constituted by an elongate housing, and a flexible and/or elastic enclosure surrounding said housing in a liquid-tight manner, further including means for supplying energy to the heat-releasing element and an axially operating first inlet at the proximal part of the housing, an outlet from the housing being arranged for the supply of heat-transmitting medium under pressure for expansion of the flexible enclosure to accommodate and to exert a controller pressure on surrounding walls of said cavity or duct, a second inlet to the housing, and a medium-actuating means for said expansion of the flexible enclosure and for internal circulation of said medium in a closed circuit from said second inlet through the housing exiting via said outlet and flowing on an outside of said housing to return to said second inlet; and a permanent non-disposable second part comprising drive means for said means for expansion and for internal circulation, and connecting means for releasably interconnecting said drive means and said means for expansion and internal circulation, said medium-actuating means comprising a first means for the expansion of the flexible enclosure, and a second means for the internal circulation of the medium through the housing, said first means being capable also of removing medium from the system to bring the enclosure into a collapsed condition.

2. An apparatus according to claim 1, wherein said second means comprises a reciprocating element creating a reciprocating motion to a determined quantity of the pressurized medium.

3. An apparatus according to claim 2, wherein said reciprocating element is part of a syringe.

4. An apparatus according to claim 1, wherein said first means is constituted by a syringe.

5. An apparatus according to claim 1, wherein said drive means comprise a first device capable of creating reciprocating motion for transfer to said reciprocating element via said connecting means.

6. An apparatus according to claim 5, wherein said device comprises an eccentric.

7. An apparatus according to claim 4, wherein said drive means additionally comprise a second drive capable of axial adjustment of an end plate of said reciprocating element via said connecting means.

8. An apparatus according to claim 7, wherein said second device is capable of providing both major adjustment, such as for filling the system under expansion of the enclosure, and fine adjustment for setting a desired pressure.

9. An apparatus according to claim 1, wherein said first means and said second device, respectively, are capable of yielding to avoid excessive pressure.

10. An apparatus according to claim 1, wherein said internal circulation allows said medium to absorb heat and subsequently release heat in said enclosure.

11. An apparatus according to claim 1, comprising at least one first back valve arranged in association with said second inlet allowing flow into the interior of housing and the flow resistance of which in an open position is lower than the flow resistance through housing, said means for internal circulation being arranged to provide a reciprocating movement of a small quantity of the pressurized medium enclosed in the inlet canal of the device after expansion of the enclosure, whereby the inlet is closed and the outlet is open, thereby providing circulation of the medium in a closed circuit.

12. An apparatus according to claim 1, comprising at least one first back valve arranged in association with the outlet allowing flow out of the interior of housing, the flow resistance of the inlet being higher than the flow resistance through housing, said means for internal circulation being arranged to provide a reciprocating movement of a small quantity of the pressurized medium enclosed in the inlet canal of the device after expansion of the enclosure, whereby the inlet is open and the outlet is closed, thereby providing circulation of the medium in a closed circuit.

13. An apparatus according to claim 1, comprising oppositely operating back valves arranged in association with said outlet and said second inlet, respectively.

14. An apparatus according to claim 1, wherein said heat-releasing element is of an inherently self-regulating type.

15. An apparatus according to claim 14, wherein said medium-actuating means comprise a first means for the expansion of the flexible enclosure, and a second means for the internal circulation of the medium through the housing.

16. An apparatus according to claim 15, wherein said first means is capable also of removing medium from the system to bring the enclosure into a collapsed condition.

17. An apparatus according to claim 15, wherein said second means comprises a reciprocating element creating a reciprocating motion to a determined quantity of the pressurized medium.

18. An apparatus according to claim 15, wherein said reciprocating element is part of a syringe.

19. An apparatus according to claim 15, wherein said first means is constituted by a syringe.

20. An apparatus according to claim 1, further comprising a second distensible and elastic enclosure, the interior of which is in communication with the interior of said flexible enclosure, whereby any undesired pressure arising in the flexible enclosure will be released through distention of said second enclosure.

21. An apparatus according to claim 20, wherein said second enclosure has a higher resistance to distention than the flexible enclosure.

22. An apparatus according to claim 20, comprising a non-elastic container surrounding said second enclosure, and means for controlling the pressure within said container and exterior to said second enclosure, whereby the level of release of said excessive pressure can be adjusted.

23. An apparatus comprising:

a disposable section including:

a first housing, substantially surrounded by a flexible enclosure, having a heat releasing element disposed therein;

tubing connected to said first housing and, said flexible enclosure at a distal end thereof;

at least one fluid pressurizing device for pumping a fluid through said tubing at a proximal end thereof and into said flexible enclosure via said first housing;

a non-disposable section including:

a second housing;

at least one retaining means within said second housing for releasably retaining said at least one fluid pressurizing device;

at least one drive means, operably connected with said at least one fluid pressurizing means when said at least one fluid pressurizing device is retained within said at least one retaining means, for powering said fluid pressurizing device to provide internal circulation of said fluid within said apparatus;

wherein said internal circulation provides for an intake of said fluid through an inlet in said first housing and moving said fluid past said heat releasing element, said fluid exiting said first housing at an outlet and returning to said inlet.

24. The apparatus of claim 23, wherein said at least one retaining means further comprises a bed for receiving said at least one fluid pressurizing device and a slot for receiving a flange associated with said at least one fluid pressurizing device.

*25. An apparatus comprising:*

*a disposable section including:*

*a first housing, substantially surrounded by a flexible enclosure;*

*tubing connected to said first housing and, said flexible enclosure at a distal end thereof;*

*at least one fluid pressurizing device for pumping a fluid through said tubing at a proximal end thereof and into said flexible enclosure via said first housing;*

*a non-disposable section including:*

*a second housing;*

*at least one retaining means within said second housing for releasably retaining said at least one fluid pressurizing device;*

*at least one drive means, operably connected with said at least one fluid pressurizing means when said at least one fluid pressurizing device is retained within said at least one retaining means, for powering said fluid pressurizing device to provide internal circulation of said fluid within said apparatus;*

*wherein said internal circulation provides for an intake of said fluid through an inlet in said first housing and moving said fluid within said flexible enclosure, said fluid exiting said first housing at an outlet and returning to said inlet.*

*26. The apparatus of claim 25, further comprising a heat releasing element.*

*27. The apparatus of claim 25, wherein the at least one drive means further comprises:*

*coarse adjustment means for filling the flexible enclosure with fluid; and*

*fine adjustment means for setting a pressure of the flexible enclosure.*

*28. The apparatus of claim 25, wherein the at least one drive means is operably connected with the at least one fluid pressurizing device by fluid control means, the fluid control means comprising:*

*means for controlling the pressure of the fluid delivered to the at least one fluid pressurizing device; and*

*means for circulating the fluid in the at least one fluid pressurizing device.*

*29. The apparatus of claim 28, wherein the means for circulating the fluid further comprises a reciprocating element for causing the fluid to circulate in the at least one fluid pressurizing device.*

*30. The apparatus of claim 28, wherein both the means for controlling the pressure and the means for circulating the fluid include a syringe.*

*31. The apparatus of claim 26, wherein heated fluid is circulated in the flexible enclosure.*

*32. An apparatus comprising:*

*a heat releasing element;*

*a disposable section including:*

*a first housing, substantially surrounded by a flexible enclosure;*

*tubing connected to said first housing and, said flexible enclosure at a distal end thereof;*

*at least one fluid pressurizing device for pumping a fluid through said tubing at a proximal end thereof and into said flexible enclosure via said first housing;*

*a non-disposable section including:*

*a second housing;*

*at least one retaining means within said second housing for releasably retaining said at least one fluid pressurizing device;*

*at least one drive means, operably connected with said at least one fluid pressurizing device when said at least one fluid pressurizing device is retained within said at least one retaining means, for powering said fluid pressurizing device to provide internal circulation of said fluid within said apparatus;*

*wherein said internal circulation provides for an intake of said fluid through an inlet in said first housing and moving said fluid past said heat releasing element, said fluid exiting said first housing at an outlet and returning to said inlet.*

*33. The apparatus of claim 32, wherein the at least one drive means is operably connected with the at least one fluid pressurizing device by fluid control means, the fluid control means comprising:*

*means for controlling the pressure of the fluid delivered to the at least one fluid pressurizing device; and*

*means for circulating the fluid in the at least one fluid pressurizing device.*

*34. The apparatus of claim 33, wherein the means for circulating the fluid further comprises a reciprocating element for causing the fluid to circulate in the at least one fluid pressurizing device.*

*35. The apparatus of claim 33, wherein both the means for controlling the pressure and the means for circulating the fluid include a syringe.*

*36. An apparatus comprising:*

*a heat releasing element;*

*a disposable section including:*

*a flexible enclosure;*

*tubing connected to said flexible enclosure at a distal end thereof;*

*at least one fluid pressurizing device for pumping a fluid through said tubing at a proximal end thereof and into said flexible enclosure;*

*a non-disposable section including:*

*a housing;*

*at least one retaining unit within said second housing for releasably retaining said at least one fluid pressurizing device;*

*at least one power unit, operably connected with said at least one fluid pressurizing device when said at least one fluid pressurizing device is retained within said at least one retaining unit, for powering said fluid pressurizing device to provide internal circulation of said fluid within said apparatus;*

*wherein said internal circulation provides for an intake of said fluid through an inlet in said fluid pressuring device and moving said fluid past said heat releasing element, said fluid exiting said fluid pressuring device at an outlet and returning to said inlet.*

*37. The apparatus of claim 36, wherein the at least one drive means is operably connected with the at least one fluid pressurizing device by fluid control means, the fluid control means comprising:*

*means for controlling the pressure of the fluid delivered to the at least one fluid pressurizing device; and*

*means for circulating the fluid in the at least one fluid pressurizing device.*

*38. The apparatus of claim 37, wherein the means for circulating the fluid further comprises a reciprocating element for causing the fluid to circulate in the at least one fluid pressurizing device.*

*39. The apparatus of claim 37 wherein both the means for controlling the pressure and the means for circulating the fluid include a syringe.*

* * * * *

UNITED STATES PATENT AND TRADEMARK OFFICE

CERTIFICATE OF CORRECTION

PATENT NO. : RE 37,651
DATED : April 9, 2002
INVENTOR(S) : Hans I. Wallstén et al.

It is certified that error appears in the above-identified patent and that said Letters Patent is hereby corrected as shown below:

Title page,
Item [22], delete "Mar. 19, 1993" and insert -- Mar. 11, 1994 --.

Signed and Sealed this

Seventh Day of October, 2003

JAMES E. ROGAN
*Director of the United States Patent and Trademark Office*